(12) United States Patent
Lips et al.

(10) Patent No.: US 10,470,662 B2
(45) Date of Patent: Nov. 12, 2019

(54) MAGNETIC RESONANCE IMAGING SYSTEM WITH INTEGRATED PHOTON DETECTOR RING

(71) Applicant: KONINKLIJKE PHILIPS N.V., Eindhoven (NL)

(72) Inventors: Oliver Lips, Eindhoven (NL); Johannes Adrianus Overweg, Eindhoven (NL); Falk Uhlemann, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 224 days.

(21) Appl. No.: 15/317,480

(22) PCT Filed: Jun. 3, 2015

(86) PCT No.: PCT/EP2015/062423
§ 371 (c)(1),
(2) Date: Dec. 9, 2016

(87) PCT Pub. No.: WO2015/197335
PCT Pub. Date: Dec. 30, 2015

(65) Prior Publication Data
US 2017/0135580 A1    May 18, 2017

(30) Foreign Application Priority Data
Jun. 23, 2014    (EP) .................................... 14173467

(51) Int. Cl.
*G01R 33/26*       (2006.01)
*A61B 5/00*        (2006.01)
(Continued)

(52) U.S. Cl.
CPC ............ *A61B 5/0035* (2013.01); *A61B 5/055* (2013.01); *A61B 6/037* (2013.01); *A61B 6/4417* (2013.01);
(Continued)

(58) Field of Classification Search
CPC ...... G01R 33/26; G01R 33/032; G01R 33/24; G01R 33/3415; G01R 33/3692; G01R 33/36; G01R 33/546
(Continued)

(56) References Cited

U.S. PATENT DOCUMENTS 5,757,188 A  *  5/1998  Miyazaki ........... G01R 33/4828
                                                      324/309
5,892,359 A      4/1999  Yui et al.
(Continued)

FOREIGN PATENT DOCUMENTS

WO    2008122899 A1    10/2008
WO    2009004521 A2     1/2009
WO    2013098699 A2     7/2013

OTHER PUBLICATIONS

Poole et al "Split Gradient Coils for Simultaneous PET-MRI" Magnetic Resonance in Medicine, vol. 62, P. 1106-1111 (2009).

*Primary Examiner* — Patrick Assouad
*Assistant Examiner* — Taqi R Nasir

(57) ABSTRACT

A magnetic resonance imaging gradient coil assembly (110) includes a cylindrical coil carrier tube (129). The cylindrical coil carrier tube has an inner surface (125) and an outer surface (129). The cylindrical coil carrier tube has a cylindrical axis of symmetry (200). The cylindrical coil carrier tube has a center (203). The cylindrical coil carrier tube has a photon detector ring receptacle (122) recessed into the inner surface of the cylindrical coil carrier tube. The detector ring receptacle is centered about the center. The photon detector ring receptacle includes side walls (126) formed
(Continued)

from the cylindrical carrier tube and a solid back wall (128) formed from the cylindrical carrier tube. The magnetic resonance imaging gradient coil assembly further includes a set of magnetic resonance imaging gradient coils (208, 210) attached to the cylindrical coil carrier tube.

20 Claims, 11 Drawing Sheets

(51) Int. Cl.
    *G01T 1/16*     (2006.01)
    *A61B 6/03*     (2006.01)
    *A61B 6/00*     (2006.01)
    *A61B 5/055*     (2006.01)
    *G01R 33/48*     (2006.01)
    *G01R 33/385*     (2006.01)

(52) U.S. Cl.
    CPC ....... *G01R 33/3856* (2013.01); *G01R 33/481* (2013.01); *G01T 1/1603* (2013.01)

(58) Field of Classification Search
    USPC .................................. 324/300, 301, 302, 304
    See application file for complete search history.

(56) References Cited

U.S. PATENT DOCUMENTS

| | | |
|---|---|---|
| 8,547,100 B2 | 10/2013 | Solf |
| 8,604,795 B2 | 12/2013 | Overweg et al. |
| 8,630,693 B2 | 1/2014 | Corbeil et al. |
| 9,442,130 B2* | 9/2016 | Karr .......................... G01T 7/00 |
| 2002/0073717 A1* | 6/2002 | Dean ....................... G01R 33/34 62/50.7 |
| 2005/0179512 A1* | 8/2005 | Weyers ............ G01R 33/34046 335/300 |
| 2009/0174407 A1* | 7/2009 | Han ................... G01R 33/3403 324/318 |
| 2009/0299170 A1 | 12/2009 | Gebhardt et al. |
| 2010/0007347 A1 | 1/2010 | Ham et al. |
| 2011/0018541 A1* | 1/2011 | Solf ..................... G01R 33/481 324/322 |
| 2011/0288401 A1 | 11/2011 | Solf et al. |
| 2014/0361181 A1* | 12/2014 | Liu ....................... G01T 1/1618 250/366 |
| 2015/0002149 A1* | 1/2015 | Nehrke ................ G01R 33/243 324/309 |

* cited by examiner

MAGNETIC RESONANCE IMAGING SYSTEM WITH INTEGRATED PHOTON DETECTOR RING

CROSS REFERENCE TO RELATED APPLICATIONS

This application is a U.S. national phase application of International Application No. PCT/EP2015/062423, filed on Jun. 3, 2015, which claims the benefit of European Patent Application No. 14173467.3 filed on Jun. 23, 2014 and is incorporated herein by reference.

TECHNICAL FIELD OF THE INVENTION

The invention relates to nuclear medical imaging techniques such as positron emission tomography or single photon emission computed tomography, in particular to the combination of nuclear medical imaging techniques with magnetic resonance imaging.

BACKGROUND OF THE INVENTION

In nuclear medical imaging techniques such as Positron Emission Tomography (PET) or Single Photon Emission Computed Tomography (SPECT) a subject ingests or is injected with a radiopharmaceutical. Typically the radiopharmaceutical comprises a radionuclide that is attached to a biologically or metabolically active molecule. A ring of photon detectors, or a photon detection ring, is placed around the subject to detect energetic photons emitted by the decay of the radio nuclide. This is then used to calculate the concentration of the radiopharmaceutical within the subject. When the radionuclide is attached to a chemical used in a metabolic process, the concentration of the radionuclide can be used to deduce physiological activity within particular tissues or organs. For example Fludeoxyglucose (18F), commonly abbreviated $^{18}$F-FDG, is a marker for the uptake of glucose by a tissue or organ. The spatial distribution of $^{18}$F-FDG can therefore be closely correlated with the metabolism of a subject.

PET and SPECT have the disadvantage that they do not provide details about the subjects internal anatomy and the response of the body to the radiopharmaceutical is relatively slow. Magnetic resonance imaging has been combined with, for example, PET to provide complementary information.

A large static magnetic field is used by Magnetic Resonance Imaging (MRI) scanners to align the nuclear spins of atoms as part of the procedure for producing images within the body of a patient. This large static magnetic field is referred to as the B0 field.

During an MRI scan, Radio Frequency (RF) pulses generated by a transmitter coil cause perturbations to the local magnetic field, and RF signals emitted by the nuclear spins are detected by a receiver coil. These RF signals can be used to deduce the concentration of certain atoms, such as hydrogen within the subject. This may be used to provide detailed information about the anatomy of the subject which can be combined with the information gained from a nuclear medical imaging technique. The chemical shifts of various resonances can also be determined to calculate the concentration of various chemical products within the subject using MRI also, using techniques referred to as functional Magnetic Resonance Imaging (fMRI). fMRI also provides data complementary to the nuclear medical imaging technique.

United Stated patent application US 2009/0299170 discloses combined MRI and PET unit. The magnet system of the MRI system is split by an azimuthal gap and the PET unit is disposed within the gap. The international application WO2008/122899 discloses a hybrid PET/MRI system. This known hybrid PET/MRI system has a split gradient coil assembly that has gradient coils connected by a stiff brace.

SUMMARY OF THE INVENTION

The invention provides for a magnetic resonance imaging gradient coil assembly and a medical instrument in the independent claims. Embodiments are given in the dependent claims.

As will be appreciated by one skilled in the art, aspects of the present invention may be embodied as an apparatus, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer executable code embodied thereon.

Any combination of one or more computer readable medium(s) may be utilized. The computer readable medium may be a computer readable signal medium or a computer readable storage medium. A 'computer-readable storage medium' as used herein encompasses any tangible storage medium which may store instructions which are executable by a processor of a computing device. The computer-readable storage medium may be referred to as a computer-readable non-transitory storage medium. The computer-readable storage medium may also be referred to as a tangible computer readable medium. In some embodiments, a computer-readable storage medium may also be able to store data which is able to be accessed by the processor of the computing device. Examples of computer-readable storage media include, but are not limited to: a floppy disk, a magnetic hard disk drive, a solid state hard disk, flash memory, a USB thumb drive, Random Access Memory (RAM), Read Only Memory (ROM), an optical disk, a magneto-optical disk, and the register file of the processor. Examples of optical disks include Compact Disks (CD) and Digital Versatile Disks (DVD), for example CD-ROM, CD-RW, CD-R, DVD-ROM, DVD-RW, or DVD-R disks. The term computer readable-storage medium also refers to various types of recording media capable of being accessed by the computer device via a network or communication link. For example a data may be retrieved over a modem, over the internet, or over a local area network. Computer executable code embodied on a computer readable medium may be transmitted using any appropriate medium, including but not limited to wireless, wire line, optical fiber cable, RF, etc., or any suitable combination of the foregoing.

A computer readable signal medium may include a propagated data signal with computer executable code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

'Computer memory' or 'memory' is an example of a computer-readable storage medium. Computer memory is any memory which is directly accessible to a processor. 'Computer storage' or 'storage' is a further example of a computer-readable storage medium. Computer storage is any non-volatile computer-readable storage medium. In some embodiments computer storage may also be computer memory or vice versa.

A 'processor' as used herein encompasses an electronic component which is able to execute a program or machine executable instruction or computer executable code. References to the computing device comprising "a processor" should be interpreted as possibly containing more than one processor or processing core. The processor may for instance be a multi-core processor. A processor may also refer to a collection of processors within a single computer system or distributed amongst multiple computer systems. The term computing device should also be interpreted to possibly refer to a collection or network of computing devices each comprising a processor or processors. The computer executable code may be executed by multiple processors that may be within the same computing device or which may even be distributed across multiple computing devices.

Computer executable code may comprise machine executable instructions or a program which causes a processor to perform an aspect of the present invention. Computer executable code for carrying out operations for aspects of the present invention may be written in any combination of one or more programming languages, including an object oriented programming language such as Java, Smalltalk, C++ or the like and conventional procedural programming languages, such as the "C" programming language or similar programming languages and compiled into machine executable instructions. In some instances the computer executable code may be in the form of a high level language or in a pre-compiled form and be used in conjunction with an interpreter which generates the machine executable instructions on the fly.

The computer executable code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Computer program instructions may be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

A 'user interface' as used herein is an interface which allows a user or operator to interact with a computer or computer system. A 'user interface' may also be referred to as a 'human interface device.' A user interface may provide information or data to the operator and/or receive information or data from the operator. A user interface may enable input from an operator to be received by the computer and may provide output to the user from the computer. In other words, the user interface may allow an operator to control or manipulate a computer and the interface may allow the computer indicate the effects of the operator's control or manipulation. The display of data or information on a display or a graphical user interface is an example of providing information to an operator. The receiving of data through a keyboard, mouse, trackball, touchpad, pointing stick, graphics tablet, joystick, gamepad, webcam, headset, wired glove, remote control, and accelerometer are all examples of user interface components which enable the receiving of information or data from an operator.

A 'hardware interface' as used herein encompasses an interface which enables the processor of a computer system to interact with and/or control an external computing device and/or apparatus. A hardware interface may allow a processor to send control signals or instructions to an external computing device and/or apparatus. A hardware interface may also enable a processor to exchange data with an external computing device and/or apparatus. Examples of a hardware interface include, but are not limited to: a universal serial bus, IEEE 1394 port, parallel port, IEEE 1284 port, serial port, RS-232 port, IEEE-488 port, Bluetooth connection, Wireless local area network connection, TCP/IP connection, Ethernet connection, control voltage interface, MIDI interface, analog input interface, and digital input interface.

A 'display' or 'display device' as used herein encompasses an output device or a user interface adapted for displaying images or data. A display may output visual, audio, and or tactile data. Examples of a display include, but are not limited to: a computer monitor, a television screen, a touch screen, tactile electronic display, Braille screen, Cathode ray tube (CRT), Storage tube, Bistable display, Electronic paper, Vector display, Flat panel display, Vacuum fluorescent display (VF), Light-emitting diode (LED) displays, Electroluminescent display (ELD), Plasma display panels (PDP), Liquid crystal display (LCD), Organic light-emitting diode displays (OLED), a projector, and Head-mounted display.

Magnetic Resonance (MR) data is defined herein as being the recorded measurements of radio frequency signals emitted by nuclear spins by the antenna of a Magnetic resonance apparatus during a magnetic resonance imaging scan. Magnetic resonance data is an example of medical image data. A Magnetic Resonance Imaging (MRI) image is defined herein as being the reconstructed two or three dimensional visualization of anatomic data contained within the magnetic resonance imaging data. This visualization can be performed using a computer.

In one aspect the invention provides for magnetic resonance imaging gradient coil assembly. The gradient coil assembly comprises a cylindrical coil carrier tube. The cylindrical coil carrier tube has an inner surface and an outer surface. The cylindrical coil carrier tube has a cylindrical axis of symmetry. The cylindrical coil carrier tube has a center. The cylindrical coil carrier tube has a photon detector ring receptacle recessed into the inner surface of the cylindrical coil carrier tube. The photon detector ring receptacle is centered about the center. The photon detector ring receptacle comprises side walls formed from the cylindrical carrier tube and a solid back wall formed from the cylindrical carrier tube. The magnetic resonance imaging gradient coil assembly further comprises a set of magnetic resonance imaging gradient coils attached to the cylindrical coil carrier tube. This embodiment may have the benefit that the photon detector ring can be incorporated more compactly with the magnetic resonance imaging gradient coil. This may save space within the bore of a magnet when it is installed into the magnet and provide more space for a subject using the magnetic resonance imaging system.

The center of the cylindrical coil carrier tube may be a mid-point of the cylindrical coil carrier tube; the mid-point may be measured on the cylindrical axis of symmetry. The center of the cylindrical coil carrier tube can also be described in terms of a symmetry plane that is perpendicular to the cylindrical axis of symmetry. For example a plane positioned half way from either end of the cylindrical coil carrier tube and perpendicular to the cylindrical axis of symmetry will define the center of the cylindrical coil carrier tube.

In another embodiment the solid back wall is solid around the entire circumference of the cylindrical coil carrier tube. In some examples there may be holes or grooves cut in the solid back wall for cabling or for coolant cable tubes.

In another embodiment the set of magnetic resonance imaging gradient coils are applied as layers on the inner surface of the cylindrical carrier tube. The set of magnetic resonance imaging gradient coils are further applied as layers on the outer surface of the cylindrical carrier tube. The set of magnetic resonance imaging gradient coils are further applied as layers on the side walls of the photon detector ring receptacle. This embodiment may have the benefit of providing for more uniform gradient fields in the vicinity of the photon detector ring.

The layer of a set of gradient coils may contain a primary X coil, a primary Y coil and a primary Z coil, which are typically applied to the inner surface of the cylindrical carrier tube. The layers of the set of gradient coil may alternatively comprise a shielded X or secondary shielding coil for the X cornet, a secondary shielding coil for the Y cornet, and a secondary shielding coil for the Z cornet. The shielding coils are typically applied to the outer surface of the cylindrical carrier tube.

The design and positioning of the coils may be accomplished by defining a set of constraints and then using a software to solve for a coil design that satisfies the constraints. The constraints could include defining the surfaces where the gradient coils will be applied as layers and then specifying a desired magnetic field. There for example exists finite difference software which can then automatically solve for the design of the gradient coils. There may be several ways of designing such a magnetic resonance imaging gradient coil assembly. One way would be to design two individual so-called split coils where the gradient coil is divided into two separate parts. Another way is to take a solid cylindrical coil carrier tube and to cut or form the photon detector ring receptacle. The layers of the set of the gradient coils may then be applied to this solid forming object. In this way wherein the cylindrical coil carrier tube is formed as an integral tube which is easy to manufacture in that there is no need to assemble the tube from various discrete components.

In another embodiment the set of magnetic resonance imaging gradient coils are further applied as layers on the solid back wall of the photon detector ring receptacle. The use of such gradient coil may result in increased homogeneity of the magnetic field generated by the gradient coils.

In another embodiment the magnetic resonance imaging gradient coil forms a split grading coil. The split gradient coil is joined by the solid back wall. A split gradient coil as used herein encompasses a magnetic field gradient coil for use in magnetic resonance imaging where the gradient coil has been divided into two separate pieces. In some embodiments the electrical connections between the two partial coils of the split gradient coil is on both faces of the solid back wall.

In another embodiment the magnetic resonance imaging gradient coil assembly comprises the photon detector ring.

In another embodiment the photon detector ring is flush with the inner surface of the cylindrical coil carrier tube. By being flush this means that the surface of the photon detector ring is at the same level as the inner surface of the cylindrical coil carrier tube. This embodiment may be beneficial because the photon detector ring does not take up any extra space than if only the magnetic resonance imaging gradient coil alone were installed. In another example the photon detector ring may be compact enough that its surface exposed to the inner bore of the magnet is within the cylindrical coil carrier tube.

In another embodiment the photon detector ring is a positron emission tomography (PET) detector ring.

In another embodiment the photon detector ring is a single photon emission computer tomography detector ring or SPECT detector ring.

In another embodiment the magnetic resonance imaging gradient coil assembly further comprises vibration dampening elements configured for supporting the photon detector ring. This may be beneficial because during the use of the gradient coils they may produce vibrations which may interfere with the photon detector ring.

In another embodiment the magnetic resonance imaging gradient coil assembly further comprises alignment pins for aligning the photon detector ring with the cylindrical coil carrier tube. This may be beneficial as it defines a geometric relationship or a physical relationship between the photon detector ring and the magnetic resonance imaging gradient coil assembly. The alignment pins may also be used for controlling the direction of the vibration of the elements or portions of the photon detector ring. For example the alignment pins may constrain the motion of the photon detector ring and the vibration dampening elements may damp this motion along the direction of the alignment pins.

In another embodiment the magnetic resonance imaging gradient coil assembly further comprises alignment elements for aligning the photon detector ring with the cylindrical coil carrier tube.

In another embodiment the magnetic resonance imaging gradient coil assembly further comprises connectors configured for connecting to the photon detector ring to provide any one of the following: electrical power, an electrical communications link, an optical communication link, coolant, air, and combinations thereof. The use of such a connector may make it convenient for removing and installing portions of the photon detector ring.

In another embodiment the connectors are attached to the side walls. Placing the connectors on the side walls may enable easy replacement or installation of the photon detector ring. The photon detector ring could be connected by one or two connectors on the side walls thus providing for more stability or support against vibrations. In one embodiment the connectors are offset from the solid back wall. This provides a space beneath the connectors where connections between the split coils can be conveniently joined.

In another embodiment the connectors are attached to the solid back wall. Placing the connectors on the solid back wall may have the advantage that the size of the detector ring along the axis of symmetry is reduced.

In another embodiment the magnetic resonance imaging gradient coil assembly comprises one or more cables to the connectors. The one or more cables comprise any one of the following: an electrical cable and a fiber optic cable. The one or more cables are any one of the following routed through the cylindrical coil carrier, routed through channels in the outer surface of the cylindrical coil carrier tube, and combinations thereof. This may be beneficial because it may provide a compact means of integrating a photon detector ring into a magnetic resonance imaging system.

In another embodiment the magnetic resonance imaging gradient coil assembly further comprises one or more coolant tubes providing the connectors with coolant. The one or more coolant tubes are any one of the following: routed through the cylindrical coil carrier tube, routed through grooves in the outer surface of the cylindrical coil carrier tube, and combinations thereof. This embodiment may be beneficial because it provides a compact means of integrating a coolant such as air, water, or other coolant into the gradient coils for cooling the photon detector ring.

The channels in the outer surface may be the same or identical with the grooves in the outer surface of the cylindrical coil carrier tube.

In another embodiment the magnetic resonance imaging gradient coil assembly comprises a manifold to distribute coolant to the set of gradient coils and to the photon detector ring. This may be beneficial because it may reduce the number of cooling devices necessary to cool both the gradient coils and the photon detector ring. The coolant may for instance be water, some other fluid, and/or air.

In another aspect the invention provides for a medical instrument. The medical instrument comprises a magnetic resonance imaging system. The magnetic resonance imaging system comprises a main magnet with a cylindrical bore. The magnetic resonance imaging system further comprises a magnetic resonance imaging gradient coil assembly according to an embodiment. The magnetic resonance imaging gradient coil assembly is located within the cylindrical bore. The medical instrument further comprises a nuclear medical imaging system. The nuclear medical imaging system comprises a photon detector ring installed into the photon detector ring receptacle of the magnetic resonance imaging gradient coil assembly. The nuclear medical imaging system may for example be a Positron Emission Tomography (PET) system or a Single Photon Emission Computed Tomography (SPECT) system.

In another aspect the invention provides for a magnetic resonance imaging system. The magnetic resonance imaging system comprises a main magnet with a cylindrical bore. The magnetic resonance imaging system further comprises a magnetic resonance imaging gradient coil assembly according to an embodiment of the invention. The magnetic resonance imaging gradient coil assembly is located or installed within the cylindrical bore of the magnet. This embodiment may be beneficial because the magnetic resonance imaging system has incorporated a positron emission tomography or SPECT system without decreasing the useable bore of the magnet. This may reduce cost because it is not necessary to get a larger magnet and/or may provide more space for patients or subjects using the magnetic resonance imaging system.

It is understood that one or more of the aforementioned embodiments of the invention may be combined as long as the combined embodiments are not mutually exclusive.

BRIEF DESCRIPTION OF THE DRAWINGS

In the following preferred embodiments of the invention will be described, by way of example only, and with reference to the drawings in which.

DETAILED DESCRIPTION OF THE EMBODIMENTS

Like numbered elements in these figures are either equivalent elements or perform the same function. Elements which have been discussed previously will not necessarily be discussed in later figures if the function is equivalent.

Figure 1:
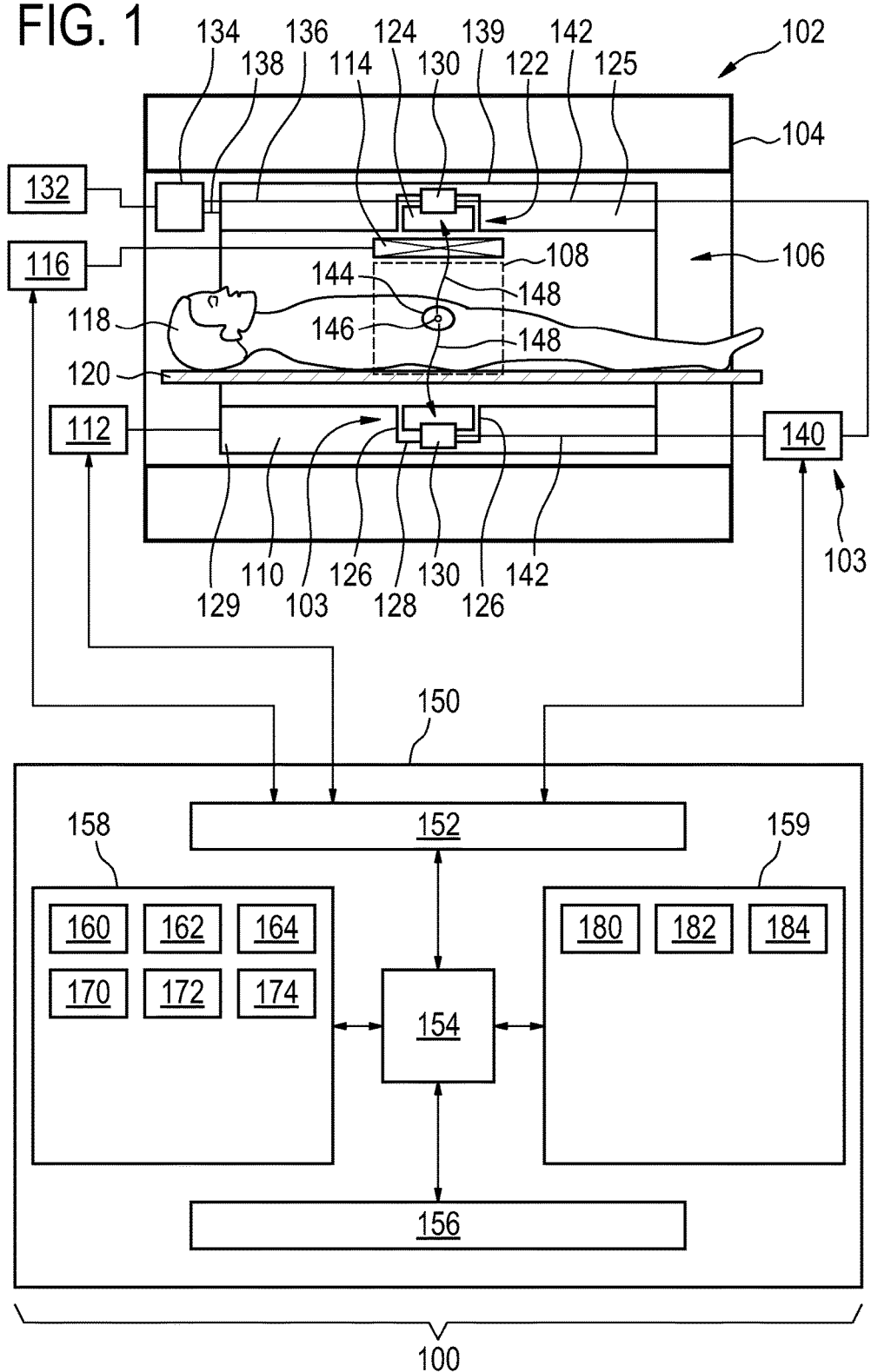
FIG. 1 illustrates an example of a medical instrument.

FIG. 1 illustrates an example of a medical instrument 100. The medical instrument 100 comprises magnetic resonance imaging system 102 with a magnet 104. The magnet 104 is a superconducting cylindrical type magnet 104 with a bore 106 through it. The use of different types of magnets is also possible for instance it is also possible to use both a split cylindrical magnet and a so called open magnet. A split cylindrical magnet is similar to a standard cylindrical magnet, except that the cryostat has been split into two sections to allow access to the iso-plane of the magnet, such magnets may for instance be used in conjunction with charged particle beam therapy. An open magnet has two magnet sections, one above the other with a space in-between that is large enough to receive a subject: the arrangement of the two sections area similar to that of a Helmholtz coil. Open magnets are popular, because the subject is less confined. Inside the cryostat of the cylindrical magnet there is a collection of superconducting coils. Within the bore 106 of the cylindrical magnet 104 there is an imaging zone 108 where the magnetic field is strong and uniform enough to perform magnetic resonance imaging.

Within the bore 106 of the magnet there is also a set of magnetic field gradient coils on a cylindrical coil carrier tube 110 which is used for acquisition of magnetic resonance data to spatially encode magnetic spins within the imaging zone 108 of the magnet 104. The magnetic field gradient coils 110 connected to a magnetic field gradient coil power supply 112. The magnetic field gradient coils 110 are intended to be representative. Typically magnetic field gradient coils 110 contain three separate sets of coils for spatially encoding in three orthogonal spatial directions. A magnetic field gradient power supply supplies current to the magnetic field gradient coils. The current supplied to the magnetic field gradient coils 110 is controlled as a function of time and may be ramped or pulsed.

Adjacent to the imaging zone 108 is a radio-frequency coil 114 for manipulating the orientations of magnetic spins within the imaging zone 108 and for receiving radio transmissions from spins also within the imaging zone 108. The radio frequency antenna may contain multiple coil elements. The radio frequency antenna may also be referred to as a channel or antenna. The radio-frequency coil 114 is connected to a radio frequency transceiver 116. The radio-frequency coil 114 and radio frequency transceiver 116 may be replaced by separate transmit and receive coils and a separate transmitter and receiver. It is understood that the radio-frequency coil 114 and the radio frequency transceiver 116 are representative. The radio-frequency coil 114 is intended to also represent a dedicated transmit antenna and a dedicated receive antenna. Likewise the transceiver 116 may also represent a separate transmitter and receivers. The radio-frequency coil 114 may also have multiple receive/transmit elements and the radio frequency transceiver 116 may have multiple receive/transmit channels.

The gradient coil 110 can be shown as having a channel cut in its mid portion which is a photon detector ring receptacle 122. The photon detector ring receptacle is shown as having a photon detector ring 124 which is installed into it and is flush with the inner surface 125 of the gradient coil 110. The photon detector ring receptacle 122 has side walls 126 and a solid back wall 128 which are formed out of a cylindrical coil carrier tube 129. There are connectors 130 which are adapted for receiving portions of the photon detector ring 124.

There is a chiller 132 which supplies coolant to a coolant manifold 134. The coolant manifold 134 supplies fluid both to a coolant connector 136 for the photon detection ring 124 and also a coolant connector 138 for the gradient coils 110. The coolant connection for the photon detector ring 136 is shown as passing through the cylindrical coil carrier tube 129. However in other examples it could be routed through an outer surface 139 of the tube 129.

The medical instrument 100 further comprises a photon detector ring electronics 140 which provides the optical and/or electrical connections for making the photon detector ring 124 function. There is shown as cabling 142 which travels from the photon detector ring electronics to the connectors 130 through the cylindrical coil carrier tube 129. In other embodiments the cabling 142 could also be routed behind on the outer surface 139.

Within imaging zone 108 the subject 118 has an organ 144 which can be imaged. The organ 144 is within the imaging zone 108. The subject 118 has also ingested or been injected with a radionuclide 146 that concentrates within the organ 144. The radionuclide 146 either emits photons or it also may emit a positron electron pair which then recombines and emits two photons 148. Photons emitted by the radionuclide 146 are then detected by the photon detector ring 124. Signals from the detectors 124 are received by the electronics 140. The electronics 140 and the photon detector ring make up a nuclear medical imaging system 103.

The transceiver 116, the magnetic field gradient coil power supply 112 and the photon detector ring electronics 140 are shown as being connected to a hardware interface 152 of computer system 150. The computer system 150 is an example of a control system or controller for controlling the medical instrument 100.

The computer system 150 is further shown as containing a processor 154. The processor 154 is further connected to the hardware interface 152, a user interface 156, computer storage 158, and computer memory 159. The contents of the computer storage 158 and the computer memory 159 may be interchanged or may be duplicated between the two.

The computer storage 158 is shown as containing pulse sequence data 160. The pulse sequence data 160 is either control commands or other data which may be converted into control commands which provide sequential instructions for the processor 154 to send to the magnetic resonance imaging system 102 to acquire magnetic resonance data 162. The computer memory 158 is shown as containing magnetic resonance data 162 of the organ 144 that was acquired using the pulse sequence data 160 to control the magnetic resonance imaging system 102. The computer storage 158 is further shown as containing a magnetic resonance image 164 that was reconstructed from the magnetic resonance data 162. The computer storage 158 is further shown as containing photon detection data 170 that was acquired using the photon detector ring 124 and the electronics 140. The computer storage further shows a nuclear medical image 172 that was reconstructed from the photon detection data 170. The computer storage 158 further shows a combined image 174 that was a combination of the nuclear medical image 172 and the magnetic resonance image 164. For instance the nuclear medical image 172 could be a positron emission tomography image which is then superimposed or combined with the magnetic resonance image 164. These images may for instance be displayed side by side on a display printed, or may be rendered together or superimposed on a screen or a display.

The computer memory 159 is shown as containing a control module. The control module 180 contains computer executable code which enables the processor 154 to control and operate the nuclear medical imaging system 103 and the magnetic resonance imaging system 102. For example the control module 180 may contain code which enables the processor 154 to execute the pulse sequence 160 to acquire the magnetic resonance data 162 and also to control the electronics 140 to acquire the photon detection data 170. The computer memory 159 is further shown as containing an image reconstruction module 182. The image reconstruction module 182 enables the processor 154 to reconstruct the magnetic resonance image 164 from the magnetic resonance data 162 and/or reconstruct the nuclear medical image 172 from the photon detection data 170. There may be additional software installed or used which enables the processor to produce the combined image 174.

Figure 2:
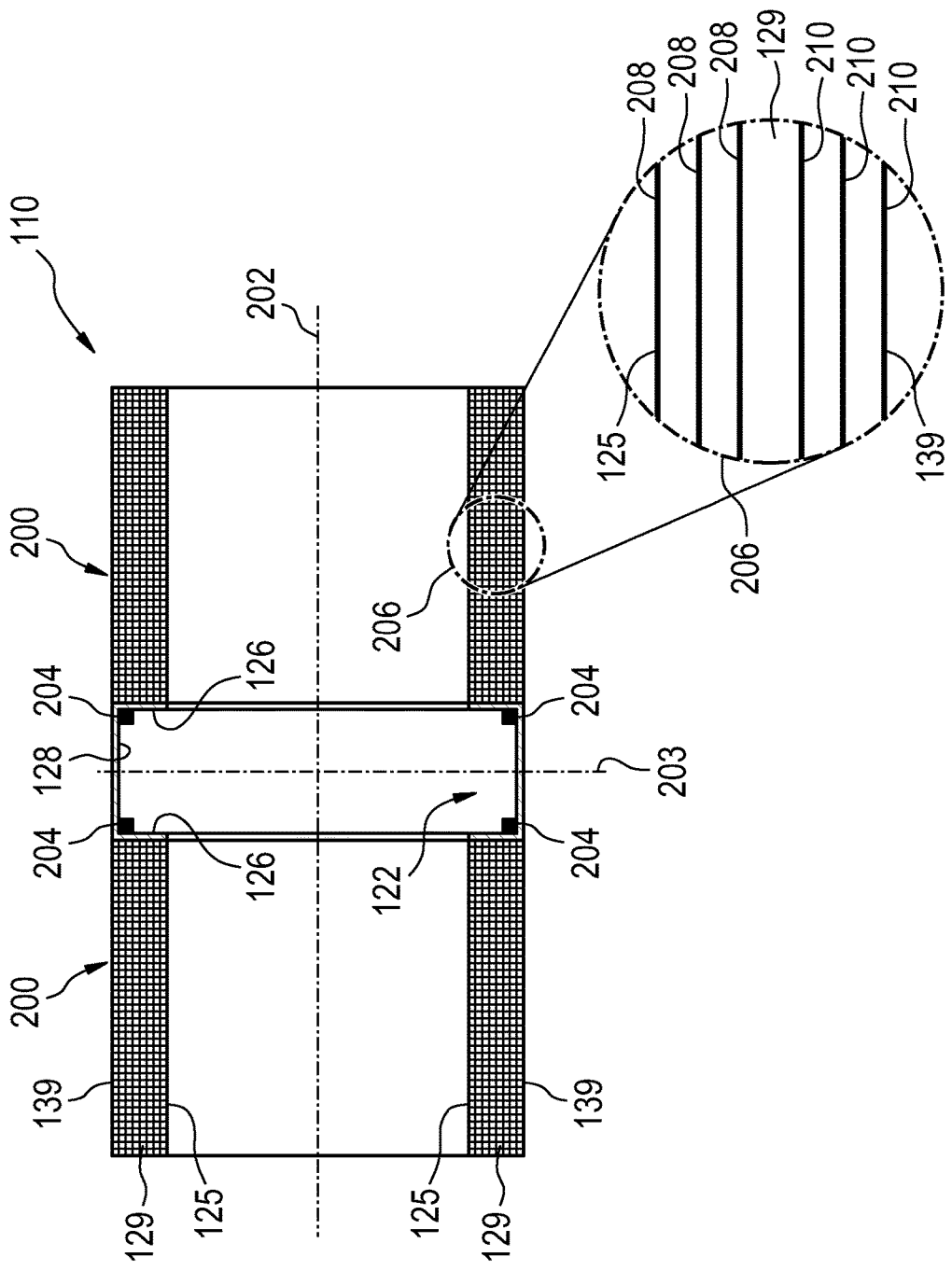
FIG. 2 illustrates an example of a magnetic resonance gradient coil assembly.

FIG. 2 shows a further example of a magnetic resonance imaging gradient coil assembly 110. In this example there are two split coil halves 200 that are joined together to form a single cylindrical coil 110. The solid back walls 128 join the two halves 200 of the gradient coil assembly. The cylindrical axis of symmetry 200 can be seen running down through the center of the cylindrical coil 110. A plane 203 perpendicular to the axis 200 and at the center point of the coil 110 defines the center of the coil 203. It can be seen that the photon detector ring receptacle 122 is centered about the central plane 203. Within the photon detector ring receptacle 122 there are a number of connections 204 which provide a space where electrical connections can be made between the two gradient coil halves 200. In some examples connectors for the photon detector ring can be placed on the side walls 126 however closer to the rotational axis 200 than the connection points 204.

Figure 3:
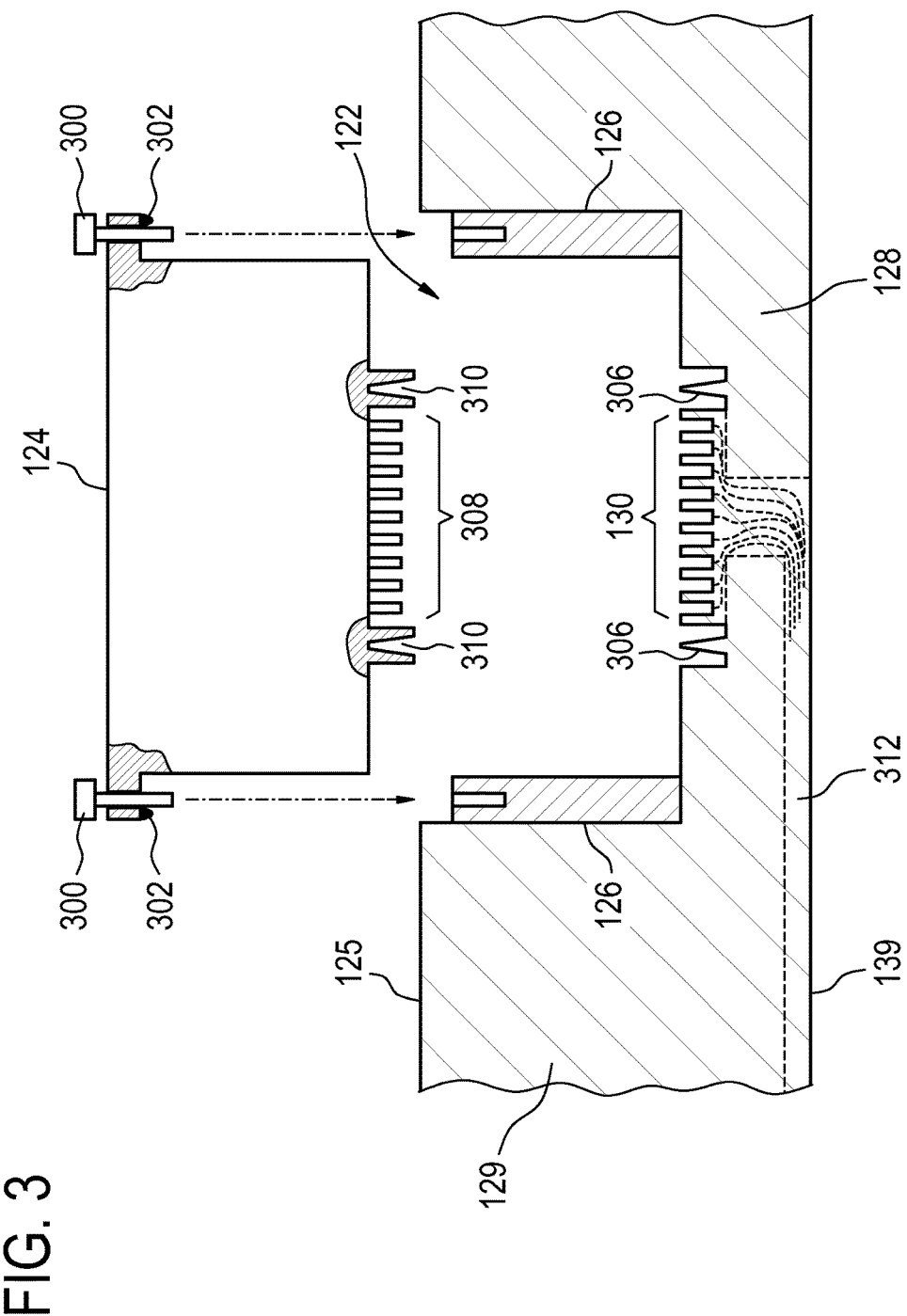
FIG. 3 illustrates a further example of a magnetic resonance gradient coil assembly.

The space for the connectors then also provides a space where the electrical connections 204 between the two coil halves 200 can be made. This may make more efficient use of the space as both the space closer and further away from the rotational axis 200 is used. There is a magnified region 206 which shows the cross-section of a gradient coil half 200 in more detail. It is seen that on the cylindrical coil carrier tube 129 there are versions of the gradient coil attached to it. Adjacent to the inner surface 125 are a number of primary coil linings 208. These are applied as layers and contain the coil for the X Y and Z gradients. On the outer surface 139 it can be seen that there are a number of secondary shielding coils 210 for the X Y and Z gradients. FIG. 3 shows a further example of a gradient coil. A cross-sectional and zoomed in view of the central region of the gradient coil is shown. The cylindrical coil carrier tube 129 is shown as having the photon detector ring receptacle 122 recessed into its center.

A module of a photon detector ring 124 is shown as being able to be installed with fasteners 300 which interlock with the side walls 126. Vibration dampening elements 302 are tensioned by the fasteners 300. The vibration dampening elements 302 support the photon detector ring 124 against the side walls 126. Recessed into the solid wall 128 is a connector 130 and several alignment pins 306. The connector 130 may supply electrical, optical, and/or coolant to the photon detector ring 124. The connector 130 mates with a connector 308 on the photon detector ring 124. Alignment pins 306 mate with alignment elements 310 on the back surface of the photon detector ring module 124. Behind the connector 130 is a space which connects with a channel or groove 312. Cabling and/or coolant tubes may be routed through the channel or groove 312 to reach the connector 130.

Figure 4:
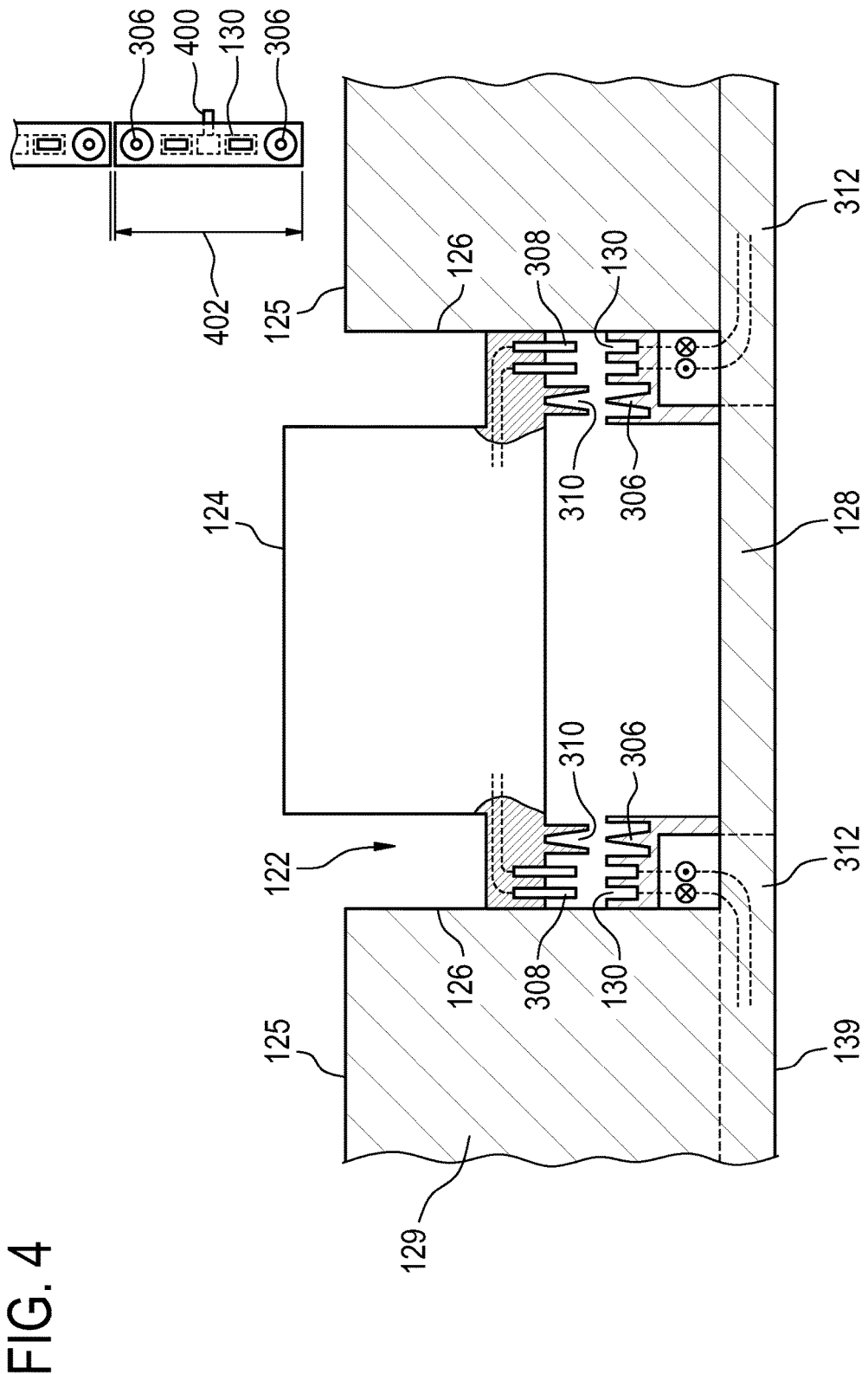
FIG. 4 illustrates a further example of a magnetic resonance gradient coil assembly.

FIG. 4 shows a further example of a gradient coil. In this example the cylindrical coil carrier tube 129 again has the photon detector ring receptacle cut into it. In this example there are connectors 130 on both side walls 126. The connectors 130 are located near the boundary between the side walls 126 and the solid back wall 128. For example electrical or optical signals could be fed from one side and cooling water could be fed from another side to keep them separate. In another example cooling water could enter from one side exits the other side and then go back and forth between several different photon detector ring modules 124. Also within FIG. 400 there is a top view 400 of the connectors 130. The space labeled by the areas 402 is the connector for one module 124. Around the circumference of the photon detector ring receptacle there are a number of connectors to which different modules 124 can be plugged into. In this example there is a channel or groove 312 on either side of the side walls 126 to provide routing for cabling and/or coolant tubes.

Figure 5:
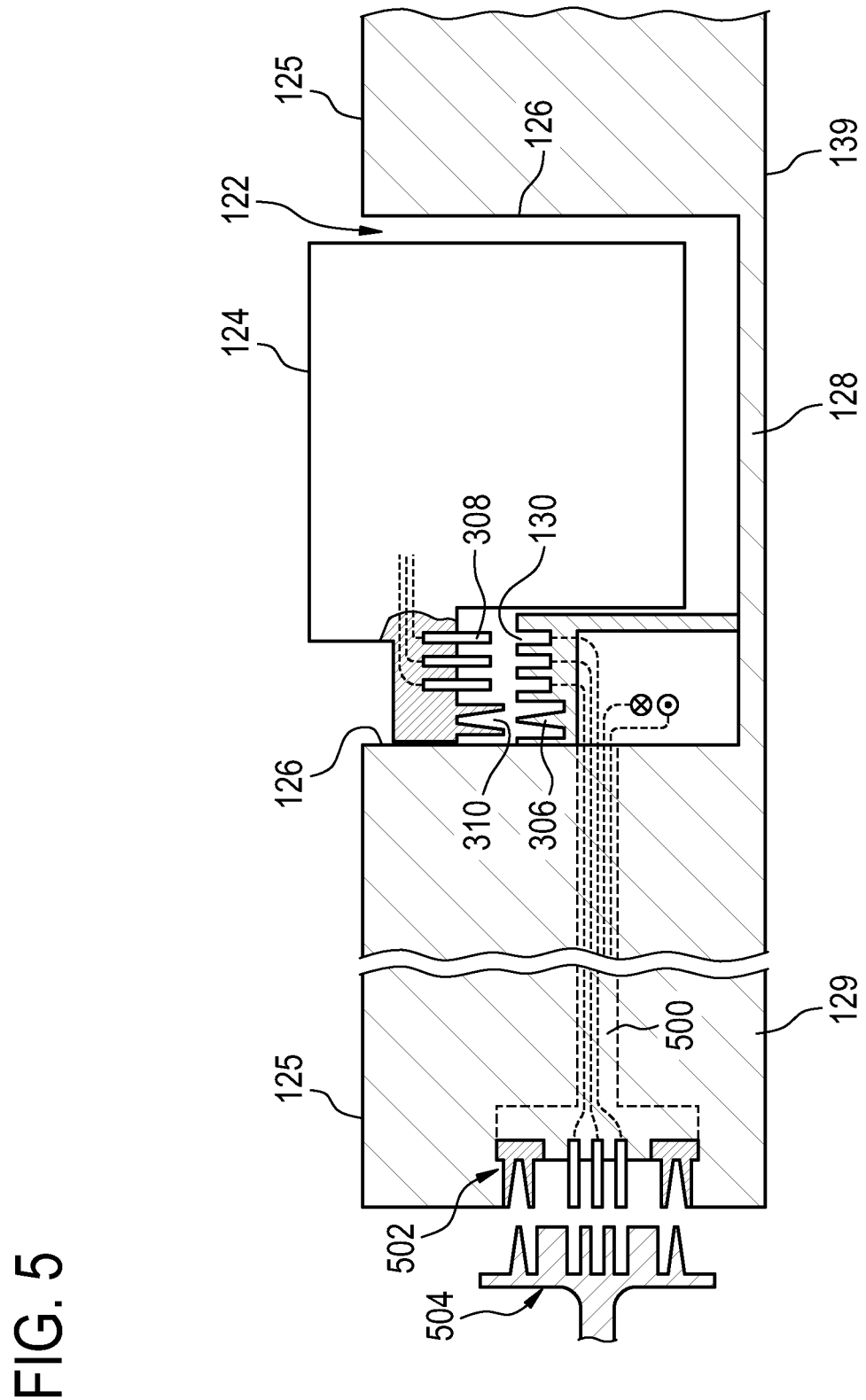
FIG. 5 illustrates a further example of a magnetic resonance gradient coil assembly.

FIG. 5 shows an example of a coil assembly similar to that that has been shown in FIGS. 3 and 4. However in this example there is one connector 130 connected to one side wall 126. There is then a hole or channel 500 cut through the cylindrical coil carrier tube which leads to a connector 502 on the edge of the in coil assembly. Another connector 504 from the SPECT or PET system can be connected to the connector 502. In another variant there are connectors on both side walls 126 in another variant once there is a connector 130 on one side wall 126 and there is a mechanical fastener on the other side wall 126. As was shown in FIG. 4 there may be a number of connectors 130 around the entire circumference of the photon detector ring receptacle 122.

Hybrid MR-PET scanners are currently gaining significant interest with the first real simultaneous devices being already available in the market. Nevertheless, combining the two distinct imaging modalities bears major technical problems. One of them is the limited space for the PET detectors inside the MR system. A major disadvantage of the current PET-MR implementations is the limited bore-size for the patient. The space for the PET detectors is gained at the expense of space for the patient. This is in particular unfavorable for oncology patients in an "arms-up" position.

Applying a split gradient coil basically allows for an increased patient space, but in the currently known implementations also some space is lost between the gradient and the RF coil, because it is needed for the connections to the PET detectors (cables, optical fibers, cooling pipes, . . . ).

The most common solution to the combine PET and MRI simultaneously currently applied is the use of a wide-bore (70 cm) MR magnet and gradient coil in combination with a small-bore (60 cm) RF coil, which creates a gap, that can accommodate the PET electronics.

In this configuration the space for the PET detectors is gained at the expense of space for the patient. This is in particular unfavorable since PET is often measured in an "arms up" position, which tends to be very uncomfortable for rather sick oncology patients in the small bore. In addition it reduces the MR field-of-view with is detrimental to the use of MR data for PET attenuation correction.

Applying a split gradient coil basically allows for an increased patient space, but in the currently known implementations also some space is lost between the gradient and the RF coil, because it is needed for the connections to the PET detectors (cables, optical fibers, cooling pipes, . . . ). Consequently an RF coil with decreased diameter has to be used, since all the connections preferably have to be routed outside the RF screen in order to avoid EM coupling and interference. The reduced RF coil diameter additionally impedes the use of "standard wide-bore" RF coil components.

Examples of the MRI imaging gradient coil assembly split gradient coil may have the benefit of accommodating the required connections to the detector modules or provides means to route these connections even outside the gradient coil. In this way the patient bore can be increased, the EM coupling of the PET connections (esp. electrical connections) to the RF coil can be reduced. Alternatively, the diameter of the gradient coil can be decreased (keeping the patient bore constant) resulting in a more efficient and cheaper gradient design.

As the gradient coil serves as a preinstalled "PET infrastructure hub" it may allows for more efficient manufacturing, installation and maintenance of the integrated PET or SPECT system.

Gradient coils are usually rigid structures, containing epoxy resin and glass fiber reinforced plastics in order to make the electrical conductors mechanically stiff and to keep them aligned. Split gradient coils are typically joined and stabilized by an outer cylindrical carrier tube to keep the coils aligned. Modifications of this carrier (or the gradient coil setup, respectively) allows for improved routing of the required connections to the PET modules. This may be done in different ways and several different examples are presented.

Figure 6:
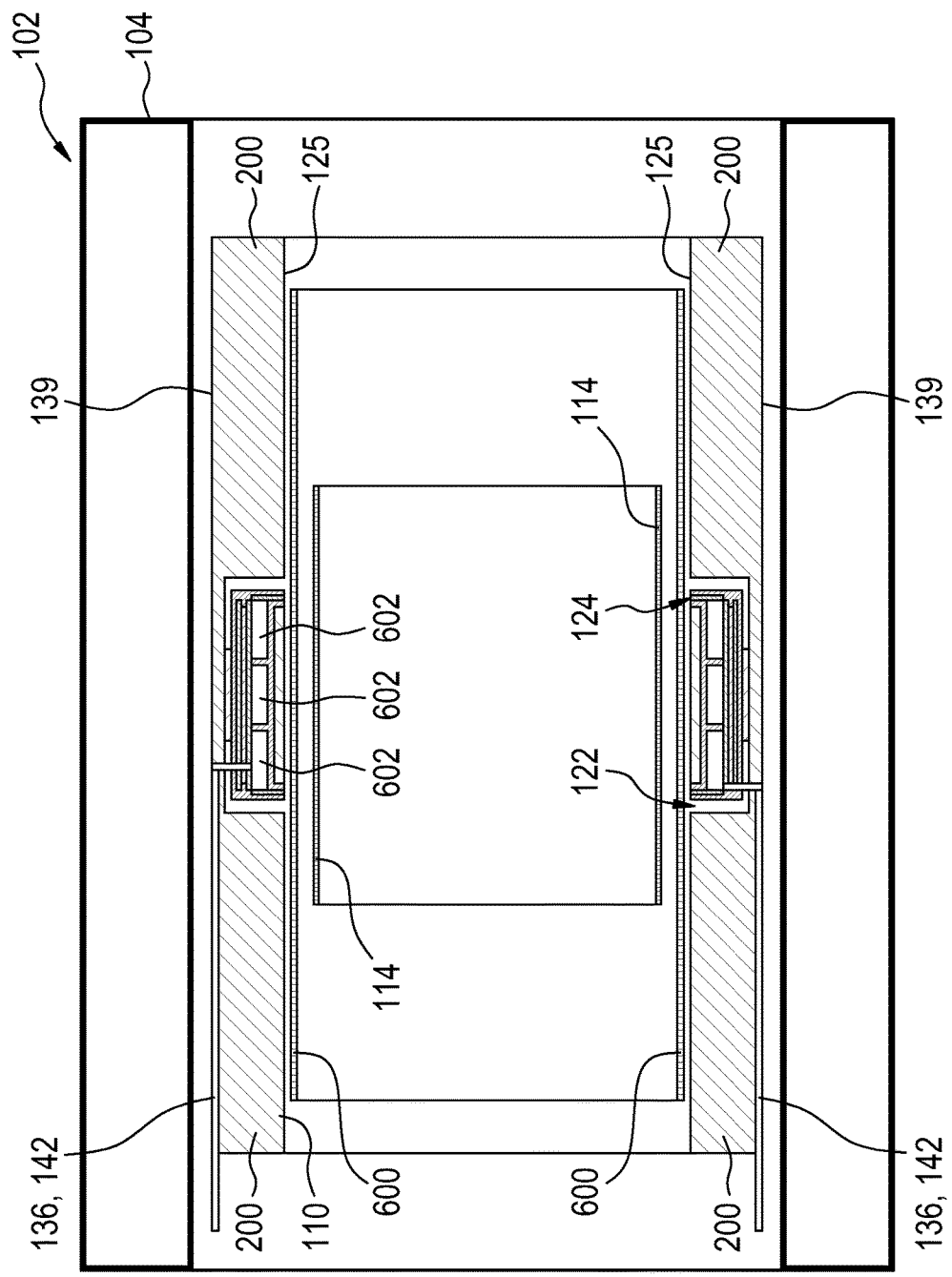
FIG. 6 illustrates an example of a magnetic resonance imaging system and a magnetic resonance gradient coil assembly.
Figure 7:
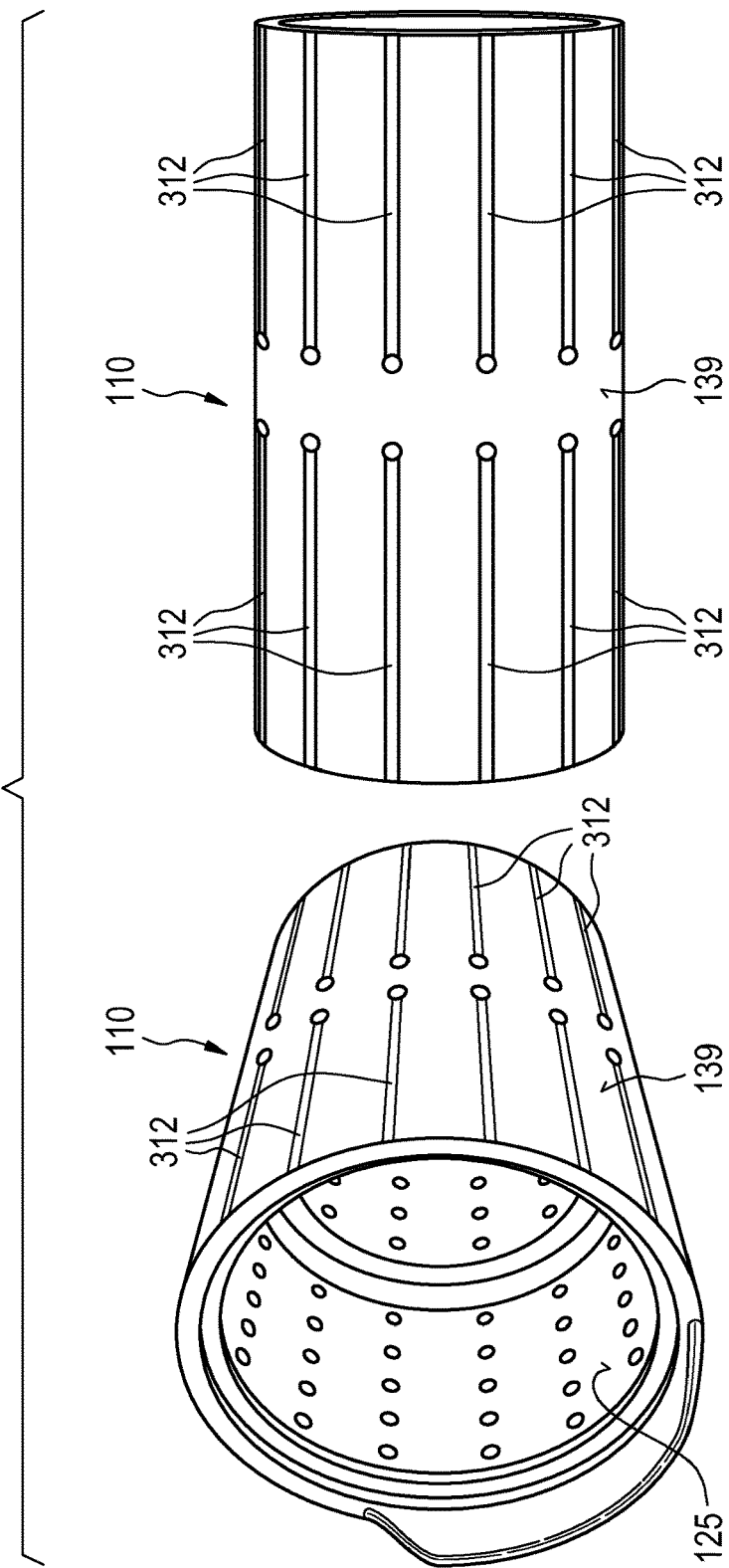
FIG. 7 further illustrates the example in FIG. 6.

In the first example PET or SPECT connections are embedded in the outer surface of the gradient coil carrier. It is possible to add about 5 mm deep grooves to the outside of the gradient coil setup without negative impact on the mechanical stability or function. These grooves can either accommodate "free" cables and pipes or these connections can be permanently integrated (glued, . . . ). FIG. 6 show examples of connections integrated into the outer surface of the gradient coil carrier. FIG. 7 shows an example with grooves on the outside of the gradient coil assembly.

FIGS. 6 and 7 illustrate an example where the outer surface 139 has channels or grooves 312 for routing the coolant connection for the photon detector rings 136 and/or the cabling 142. A radio frequency screen 600 can also be seen as being between the RF coil 114 and the gradient coil assembly 110. The photon detector ring modules 124 can also be seen as having multiple scintillators 602 within them.

Figure 8:
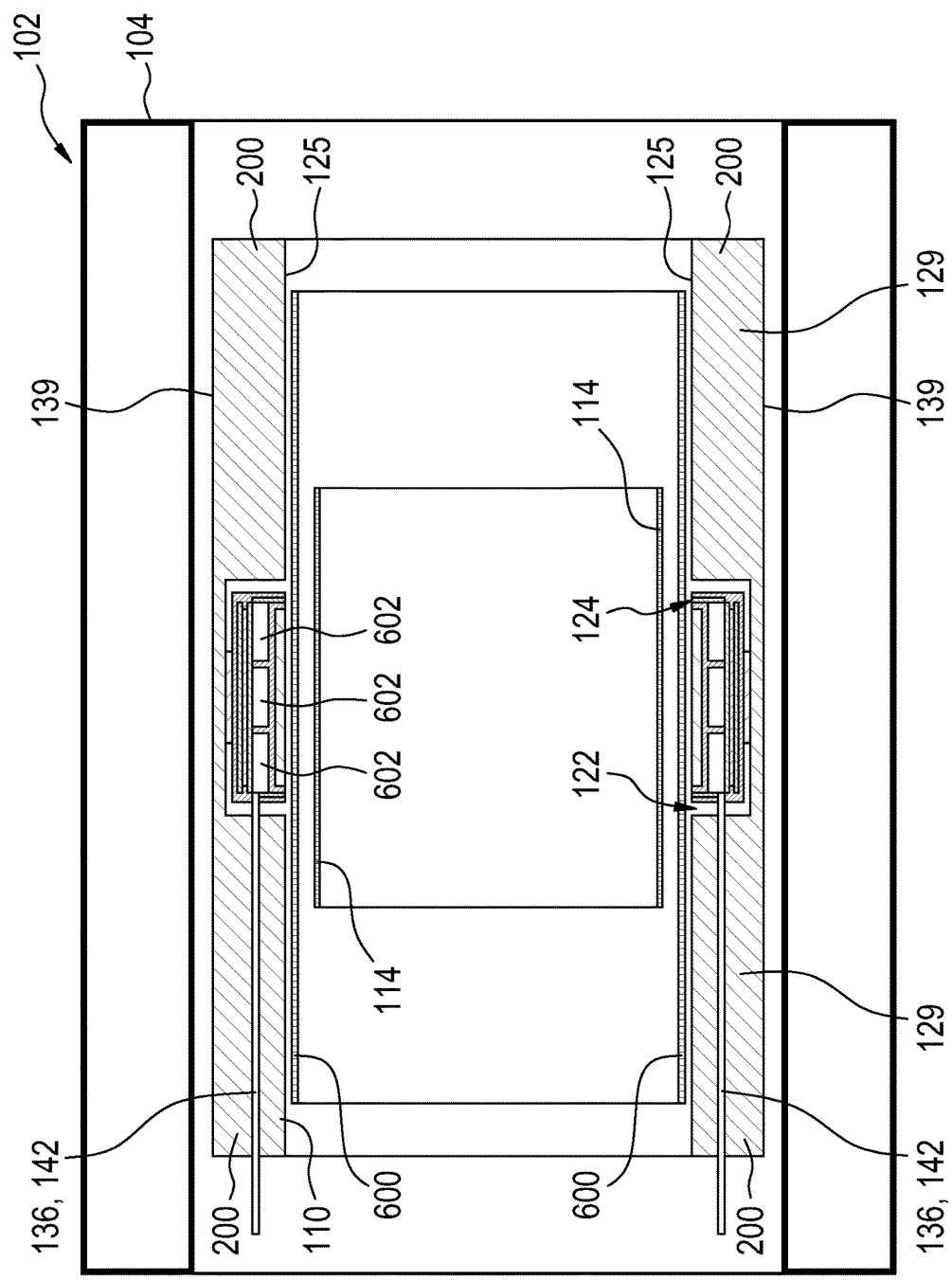
FIG. 8 illustrates a further example of a magnetic resonance imaging system and a magnetic resonance gradient coil assembly.
Figure 9:
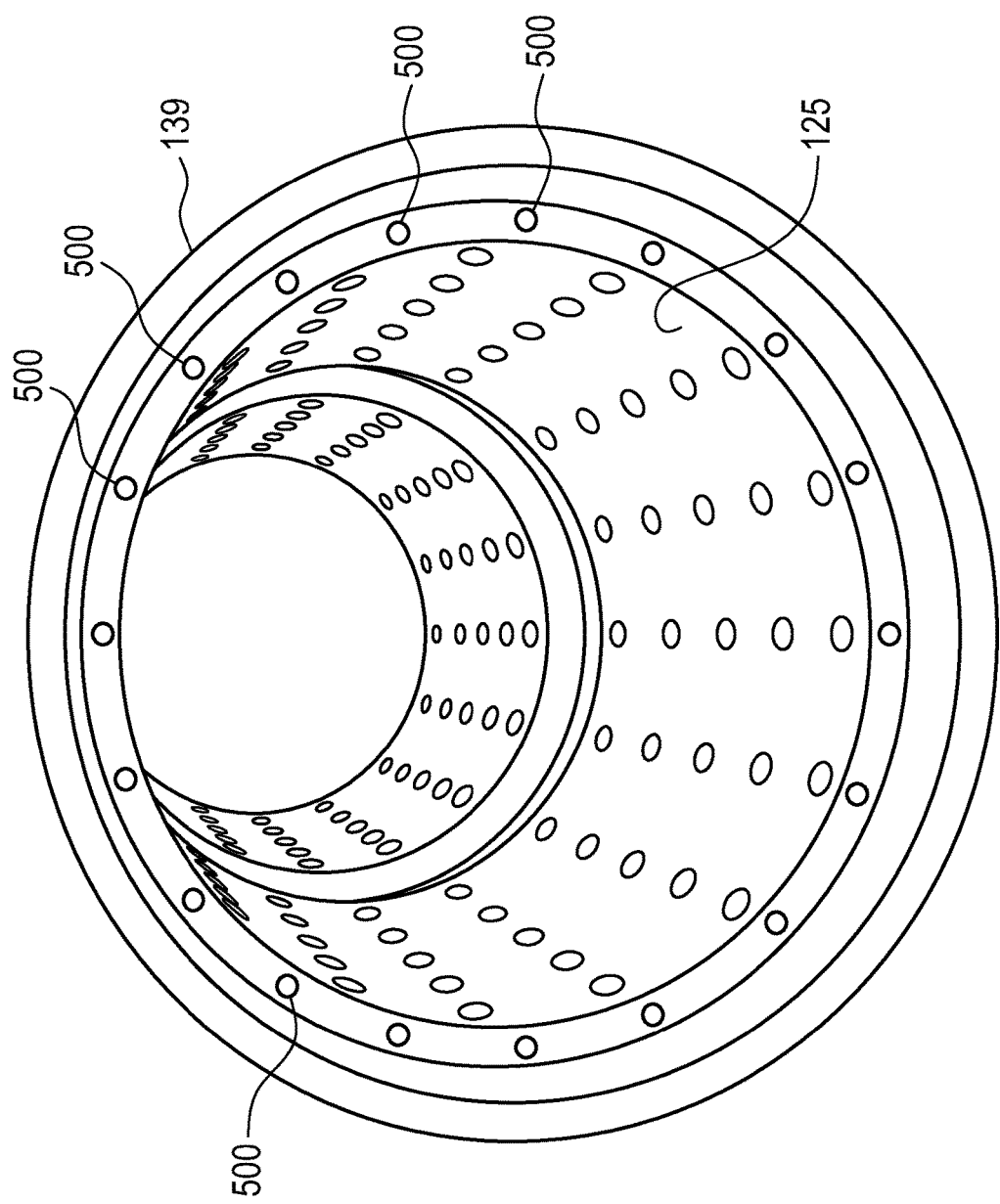
FIG. 9 further illustrates the example of FIG. 8.

In a second example, PET or SPECT connections are fed through channels implemented into the gradient coil (between primary and secondary coil). At certain positions, where there are no conductors at the front/back sides, or where the conductors are wide enough to add a hole into them, it seems possible to integrate the required channels into the gradient coil. FIG. 8 shows an example with channels in the gradient coil (between primary and secondary windings). FIG. 9 also shows an example with channels through the gradient coil assembly FIGS. 8 and 9 illustrate a variant of a gradient coil assembly 110 that is similar to that shown in FIGS. 6 and 7. The difference in these two Figs. is that the coolant connection for the photon detector rings 136 and the cabling 142 are routed through holes 500 through the cylindrical coil carrier tube 129.

Figure 10:
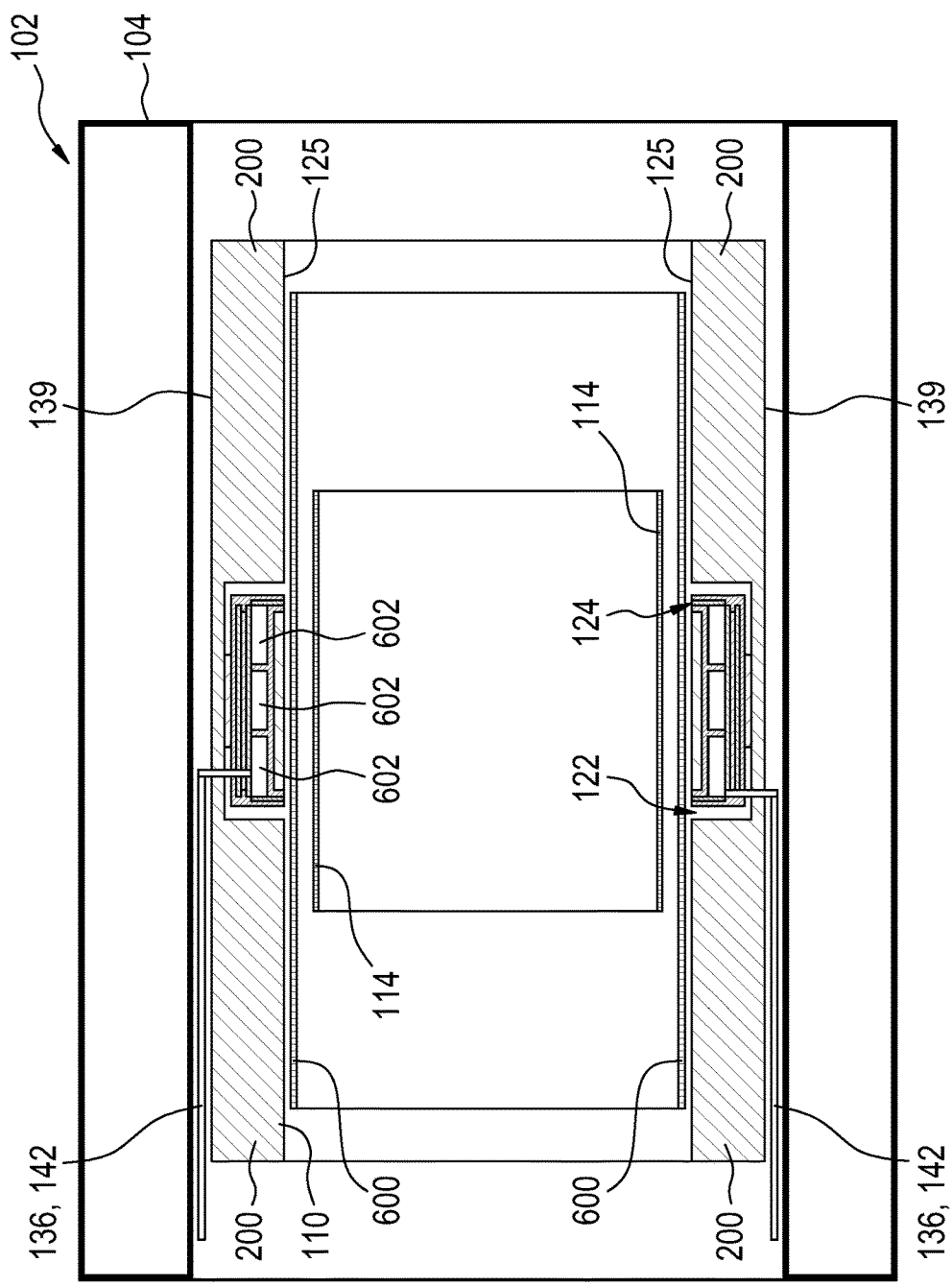
FIG. 10 illustrates a further example of a magnetic resonance imaging system and a magnetic resonance gradient coil assembly.
Figure 11:
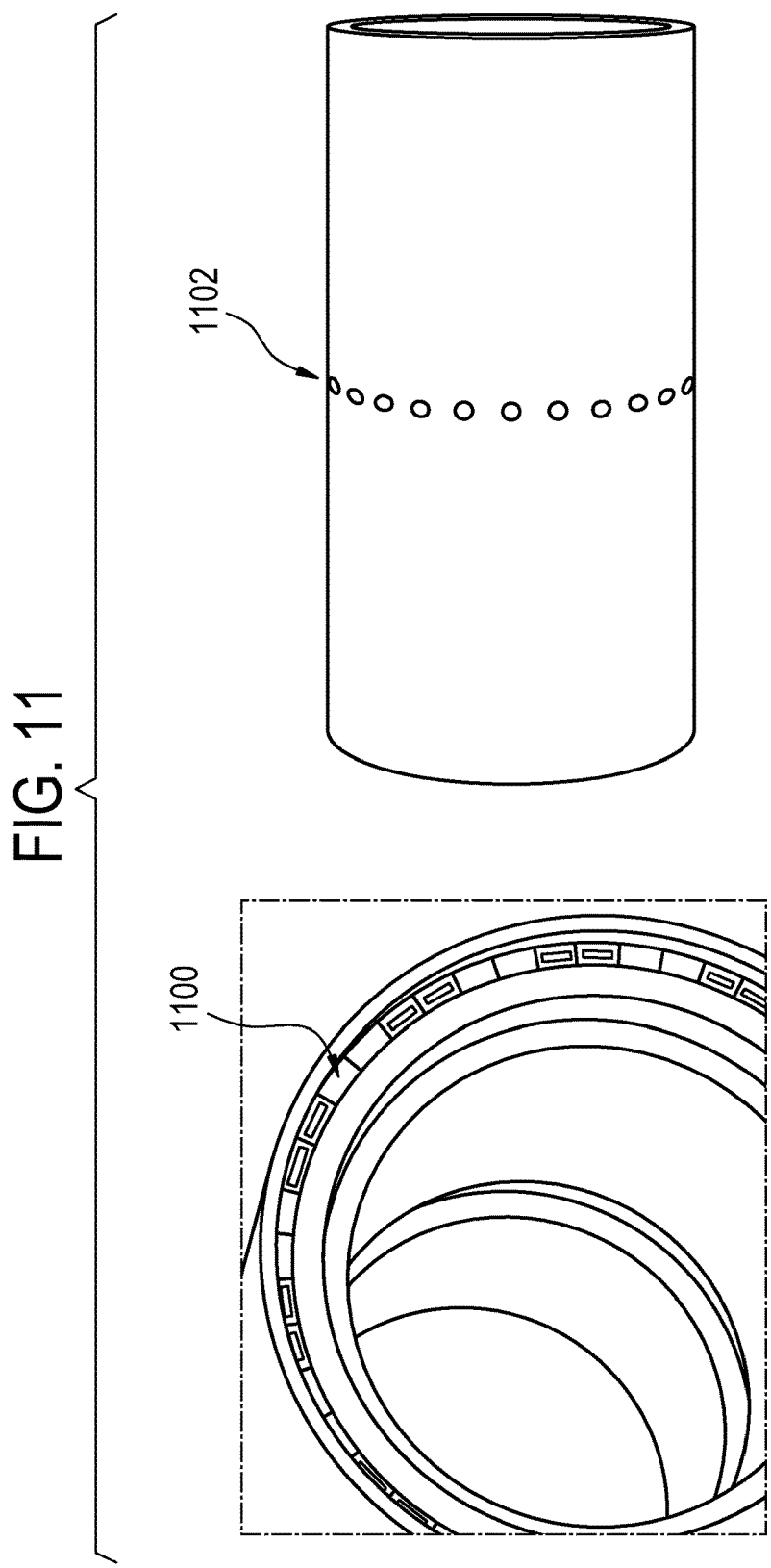
FIG. 11 further illustrates the example of FIG. 10.

In a third example, the cylindrical coil carrier tube has feed-throughs in the middle part in order to allow for connecting the PET modules with cables and pipes routed outside the gradient coil (in the gap to the magnet). FIG. 10 shows an example with feed-throughs in the middle of the gradient coil carrier tube and routing of the cables/pipes outside the gradient coil assembly. FIG. 11 shows an example with feed-throughs in the middle of the gradient coil and routing of the cables/pipes outside the gradient coil assembly.

FIGS. 10 and 11 are used to illustrate a further example of a gradient coil assembly 110. In this example there are feed-throughs in the middle of the gradient coil and the routing of the coolant tubes 136 or the cabling 142 is done outside of the gradient coil assembly 110. The arrows labeled 1100 indicates where connections are routed outside of the gradient coil assembly. The arrows labeled 1102 indicate where feed-throughs into the split part of the gradient coil for cabling or coolant tubes to pass through.

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

LIST OF REFERENCE NUMERALS 100 medical instrument
102 magnetic resonance imaging system
103 nuclear medical imaging system
104 magnet
106 bore of magnet
108 imaging zone
110 magnetic field gradient coils
112 magnetic field gradient coil power supply
114 radio-frequency coil
116 transceiver
118 subject
120 subject support
122 photon detector ring receptacle
124 photon detector ring
125 inner surface
126 side walls
128 solid back wall
129 cylindrical coil carrier tube
130 connector
132 chiller
134 coolant manifold
136 coolant connection for photon detector ring
138 coolant connector for gradient coils
139 outer surface
140 photon detector ring electronics
142 cabling
144 organ
146 concentration of radionuclide
148 photon emission
150 computer system
152 hardware interface
154 processor
156 user interface
158 computer storage
159 computer memory
160 pulse sequence data
162 magnetic resonance data
164 magnetic resonance image
170 photon detection data
172 nuclear medical image
174 combined image
180 control module
182 image reconstruction module
200 split coil half
202 cylindrical axis of symmetry
203 center of coil
204 connections between coil halves
206 magnified region
208 primary coil
210 secondary shielding coil
300 fasteners
302 vibration dampening element
306 alignment pin
308 connector
310 alignment element
312 channel or groove
400 top view of connectors
402 connector for one module
500 hole 502 connector
504 connector
600 RF screen
602 multiple scintillators
1100 connections routed outside of gradient coil assembly
1102 feed-throughs into split part of gradient coil

The invention claimed is:

1. A magnetic resonance imaging gradient coil assembly comprising:
a cylindrical coil carrier tube, wherein the cylindrical coil carrier tube has an inner surface and an outer surface, where the cylindrical coil carrier tube has a cylindrical axis of symmetry, wherein the cylindrical coil carrier tube has a center, wherein the cylindrical coil carrier tube has a photon detector ring receptacle recessed into the inner surface of the cylindrical coil carrier tube, wherein the photon detector ring receptacle is centered about the center, wherein the photon detector ring receptacle comprises side walls formed from the cylindrical carrier tube and a solid back wall formed from the cylindrical carrier tube; and
a set of magnetic resonance imaging gradient coils attached to the cylindrical coil carrier tube wherein the magnetic resonance imaging gradient coil assembly further comprises connectors configured for connecting one or more cables to a photon detector ring received in the photon detector ring receptacle;
wherein the one or more cables are, routed at least for a part through channels in the outer surface of the cylindrical coil carrier tube.

2. The magnetic resonance imaging gradient coil assembly of claim 1, wherein the connectors are plug and socket connectors.

3. The magnetic resonance imaging gradient coil assembly of claim 1, wherein the set of magnetic resonance imaging gradient coils are applied as layers on: the inner surface of the cylindrical carrier tube, the outer surface of the cylindrical carrier tube, and the side walls of the photon detector ring receptacle.

4. The magnetic resonance imaging gradient coil assembly of claim 1, wherein the magnetic resonance imaging gradient coils form a split gradient coil, wherein the split gradient coil is joined by the solid back wall.

5. A medical instrument comprising:
a magnetic resonance imaging system, wherein the magnetic resonance imaging system comprises a main magnet with a cylindrical bore, wherein the magnetic resonance imaging system further comprises a magnetic resonance imaging gradient coil assembly according to claim 2, wherein the magnetic resonance imaging gradient coil assembly is located within the cylindrical bore; and
a nuclear medical imaging system, wherein the nuclear medical imaging system comprises a photon detector ring installed into the photon detector ring receptacle of the magnetic resonance imaging gradient coil assembly.

6. A magnetic resonance imaging gradient coil assembly comprising:
a cylindrical coil carrier tube, wherein the cylindrical coil carrier tube has an inner surface and an outer surface, where the cylindrical coil carrier tube has a cylindrical axis of symmetry, wherein the cylindrical coil carrier tube has a center, wherein the cylindrical coil carrier tube has a photon detector ring receptacle recessed into the inner surface of the cylindrical coil carrier tube, wherein the photon detector ring receptacle is centered about the center, wherein the photon detector ring receptacle comprises side walls formed from the cylindrical carrier tube and a solid back wall formed from the cylindrical carrier tube; and
a set of magnetic resonance imaging gradient coils attached to the cylindrical coil carrier tube wherein the magnetic resonance imaging gradient coil assembly further comprises connectors configured for connecting one or more cables to a photon detector ring wherein the connectors are plug and socket connectors;
wherein the one or more cables are routed at least for a part through channels in the outer surface of the cylindrical coil carrier tube, wherein the channels extend longitudinally along the cylindrical coil carrier tube.

7. The magnetic resonance imaging gradient coil assembly of claim 6, wherein the magnetic resonance imaging gradient coil assembly comprises a photon detector ring accommodated in the photon detector ring receptacle.

8. The magnetic resonance imaging gradient coils assembly of claim 7, wherein the photon detector ring is flush with the inner surface of the cylindrical coil carrier tube.

9. The magnetic resonance imaging gradient coils assembly of claim 7, wherein the photon detector ring is a PET or a SPECT detector ring.

10. The magnetic resonance imaging gradient coil assembly of claim 7, wherein the magnetic resonance imaging gradient coil assembly further comprises the following: vibration dampening elements configured for supporting the photon detector ring, and alignment pins for aligning modules of the photon detector ring with the cylindrical coil carrier tube.

11. The magnetic resonance imaging gradient coil assembly of claim 7, wherein the connectors are configured for connecting to the photon detector ring to provide any one of the following: electrical power, an electrical communication link, an optical communication link, coolant, air, and combinations thereof.

12. The magnet resonance imaging gradient coil assembly of claim 7, wherein the one or more cables comprises any one of the following: an electrical cable, a fiber optic cable, and combinations thereof.

13. A magnetic resonance imaging gradient coil assembly, comprising:
a cylindrical coil carrier tube, wherein the cylindrical coil carrier tube has an inner surface and an outer surface, where the cylindrical coil carrier tube has a cylindrical axis of symmetry, wherein the cylindrical coil carrier tube has a center, wherein the cylindrical coil carrier tube has a photon detector ring receptacle recessed into the inner surface of the cylindrical coil carrier tube, wherein the photon detector ring receptacle is centered about the center, wherein the photon detector ring receptacle comprises side walls formed from the cylindrical carrier tube and a solid back wall formed from the cylindrical carrier tube; and
a set of magnetic resonance imaging gradient coils attached to the cylindrical coil carrier tube;
a photon detector ring received in the photodetector ring receptacle, wherein the photon detector ring includes a plurality of photon detector ring modules, each of the photon detector ring modules including at least one photon detector module connector;
wherein a plurality of photon detector ring receptacle connectors are mounted on side and/or rear walls of the photon detector ring receptacle wherein the photon detector module connectors and the photon detector ring receptacle connectors are plug and socket connectors, such that the photon detector module connectors of each detector ring module are configured to be plugged into a corresponding photon detector ring receptacle connector mounted to the rear or side wall of the photon detector ring receptacle;

wherein the photon detector ring modules connectors are configured for connecting one or more cables to the photon detector ring;

wherein the one or more cables are routed at least for a part through channels defined in and extending longitudinally along the outer surface of the cylindrical coil carrier tube.

14. The magnetic resonance imaging gradient coil assembly of claim 13, wherein the photon detector ring receptacle connectors are attached to side walls of the photon detector ring receptacle.

15. The magnetic resonance imaging gradient coil assembly of claim 13, wherein the photon detector ring receptacle connectors are attached to the solid back wall.

16. The magnet resonance imaging gradient coil assembly of claim 13, wherein the magnet resonance imaging gradient coil assembly comprises one or more coolant tubes for providing the photon detector ring modules with coolant via the photon detector ring receptacle connectors and the photon detector ring module connector, wherein the one or more coolant tubes are any one of the following: routed through the cylindrical coil carrier tube, routed through grooves in the outer surface of the cylindrical coil carrier tube, and combinations thereof.

17. The magnet resonance imaging gradient coil assembly of claim 16, wherein the magnet resonance imaging gradient coil assembly comprises a manifold to distribute coolant to the set of gradient coils and to each of the photon detector ring modules.

18. The magnetic resonance imaging gradient coil of claim 13, wherein one of the photon detector module connectors and the photon detector ring receptacle connectors includes a pin and the other includes an alignment element, the pins and the alignment elements inter-engaging to align the photon detector module connectors and the photon detector ring receptacle connectors.

19. The magnetic resonance imaging gradient coil assembly of claim 18, further including:

fasteners configured to fasten each photon detector module in the photon detector ring receptacle.

20. The magnetic resonance imaging gradient coil assembly of claim 13, further including electrical or fiber optic cables connected with the photon detector ring receptacle connectors and extending through the coil carrier tube to a carrier tube plug or socket connector mounted with the coil carrier tube.

* * * * *